United States Patent [19]

Bryant

[11] Patent Number: 5,201,712
[45] Date of Patent: Apr. 13, 1993

[54] CATHETER ASSEMBLY WITH RECIPROCABLE OBTURATOR

[75] Inventor: Peter L. Bryant, Libertyville, Ill.

[73] Assignee: Abbott Laboratories, Abbott Park, Ill.

[21] Appl. No.: 762,701

[22] Filed: Sep. 19, 1991

[51] Int. Cl.$^5$ .................................. A61M 5/178
[52] U.S. Cl. .................. 604/164; 604/166; 604/256
[58] Field of Search ............ 604/164, 166, 170–171, 604/264, 271, 158, 160, 256

[56] References Cited

U.S. PATENT DOCUMENTS

| | | | |
|---|---|---|---|
| 3,856,009 | 12/1974 | Winnie | 604/164 |
| 4,798,591 | 1/1989 | Okada | 604/164 |
| 4,803,999 | 2/1989 | Liegner | 128/763 |
| 4,976,697 | 12/1990 | Walder et al. | 604/164 |
| 5,030,227 | 7/1991 | Rosenbluth et al. | 606/192 |
| 5,135,525 | 8/1992 | Biscoping et al. | 604/51 |

FOREIGN PATENT DOCUMENTS 142879 11/1953 Sweden .................. 604/256

Primary Examiner—C. Fred Rosenbaum
Assistant Examiner—C. Maglione
Attorney, Agent, or Firm—A. Nicholas Trausch; Thomas M. Breininger

[57] ABSTRACT

A catheter assembly with a reciprocable obturator is disclosed which facilitates patency maintenance during intravenous therapy. The assembly includes a catheter having an elongated tubular portion defining a lumen, and an obturator assembly mounted on the catheter. The obturator assembly includes a reciprocable obturator member including an elongated obturator rod telescopically disposed within the catheter lumen. The rod is configured to cooperate with the lumen to inhibit liquid flow into the free end of the catheter. The device can be employed in conjunction with a high molecular weight, viscous fluid, in order to further inhibit ingress of liquid into the catheter.

7 Claims, 1 Drawing Sheet

CATHETER ASSEMBLY WITH RECIPROCABLE OBTURATOR

TECHNICAL FIELD

The present invention relates generally to catheter assemblies for intravenous therapy, and more particularly to a catheter assembly including a selectively positionable, valve like obturator which is effective to maintain the patency of the catheter assembly during periods between infusions with the assembly.

BACKGROUND OF THE INVENTION

Intravenous therapy employing catheter assemblies frequently requires that the patency, or open condition of the catheter, be maintained during periods between infusion of nutritional or therapeutic solutions. In the past, several different approaches have been taken for achieving patency maintenance, with varying degrees of effectiveness.

One approach, usually referred to as KVO, or "keep vein open", entails substantially continuously infusing a non-therapeutic solution, such as saline, into the patient. Flow rates on the order of 5–125 milliliters per hour are typical, and can be effected by either gravity-flow or infusion pump systems. While this type of therapy is generally regarded as effective for patency maintenance, it will be appreciated that the essentially uninterrupted nature of the therapy results in relatively high cost, as well as the infusion of liquid which might otherwise not be required by the patient.

Alternate approaches entail formation of solution "locks" by essentially flooding the catheter with a non-therapeutic solution between infusions. The use of heparin, an anti-coagulant, as a fluid lock is generally regarded as effective for patency maintenance, with the added advantages, compared to KVO therapy, of patient mobility, minimal nursing attention, and minimal fluid introduction to the patient. On balance, the use of a heparin lock has the disadvantages of the attendant "SASH" procedure (flush with saline, infusion with antibiotic, followed by saline flush, and reestablishment of the heparin lock), as well as the potential incompatibility of heparin with many antibiotic solutions.

Alternately, saline locks can be employed, with the saline substituted for the heparin solution in the catheter. However, the effectiveness of saline locks is generally regarded to be less than that of the aforementioned patency maintenance techniques.

Consistent and cost-effective patency maintenance is desirable for efficient intravenous therapy. The present invention contemplates a desirably straightforward patency maintenance arrangement which specifically addresses the drawbacks associated with currently used techniques.

SUMMARY OF THE INVENTION

The present invention is directed to a catheter assembly with a reciprocable obturator mounted thereon for cooperation with the lumen of the catheter. The obturator functions in a valve-like manner to close and substantially seal the free end of the catheter between infusions. If desired, the assembly can be supplied with a high molecular weight, viscous fluid, to further prevent blood from entering the catheter lumen and causing patency loss. Because the obturator is configured for selective positioning relative to the catheter, the assembly can be operated to open the catheter the permit the infusion of therapeutic or nutritional solutions as necessary.

In accordance with the illustrated embodiment, the present assembly comprises a catheter including a base portion, and a tubular portion extending from the base portion and defining a lumen in fluid communication with an interior defined by the base portion.

An obturator assembly, which may be alternately employed with an existing catheter, or supplied preassembled with a catheter, is mounted on the catheter for controlling liquid flow into the lumen at the free end of the tubular portion of the catheter. The obturator assembly includes a reciprocable obturator member including an elongated obturator rod, which extends telescopically within the lumen of the tubular portion of the catheter. The obturator rod is arranged for selective, reciprocable movement axially of the tubular portion of the catheter between first and second positions. In the first, closed position of the obturator rod, it cooperates with the tubular portion of the catheter in a valve-like manner to inhibit flow of liquid into the free end of the tubular portion. In the second, open position of the rod, liquid can flow through the lumen of the tubular portion and past the obturator rod. A biasing arrangement is preferably provided for biasing the obturator rod toward the first, closed position thereof.

To provide the desired valve-like action, the free end portion of the obturator rod is of a circular configuration complemental to the lumen of the tubular portion of the catheter. In this way, the free end portion of the rod cooperates with the tubular portion for inhibiting liquid flow into the lumen. In order to accommodate flow through the lumen, the obturator rod defines at least one groove or recess which extends axially of the rod within the tubular portion. In the illustrated form, the obturator rod has a multi-lobular cross-sectional configuration inwardly of the free end portion thereof, to thereby define a plurality of grooves corresponding in number to the number of lobes of the cross-sectional configuration of the rod.

By this arrangement, the obturator rod is positionable in its first position for closing the catheter, in which position the rod is retracted within the lumen, and the free end portion of the rod closes the lumen. When the rod is extended relative to the catheter, the free end portion of the rod is moved out of cooperation with the lumen, whereby the grooves in the rod are exposed to permit liquid flow through the tubular portion of the catheter and past the obturator rod.

Other features and advantages of the present invention will become readily apparent from the following detailed description, the accompanying drawings, and the appended claims.

DETAILED DESCRIPTION

Figure 1:
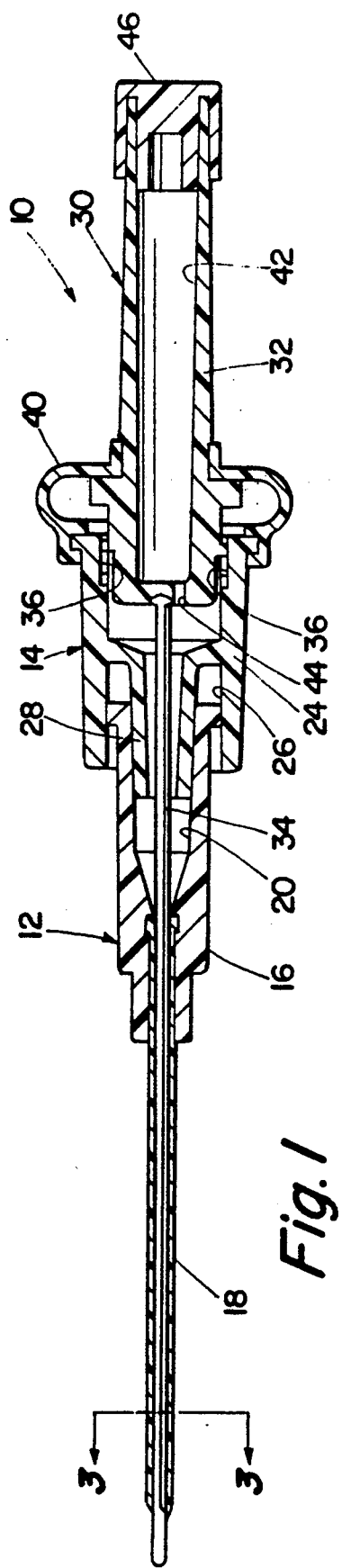
FIG. 1 is a diagrammatic, cross-sectional view illustrating a catheter assembly in accordance with the present invention.

While the present invention is susceptible of embodiment in various forms, there is shown in the drawings and will hereinafter be described a presently preferred embodiment, with the understanding that the present disclosure is to be considered as an exemplification of the invention, and is not intended to limit the invention to the specific embodiment illustrated.

With reference now to the drawings, therein is illustrated a catheter assembly 10 including a reciprocable obturator embodying the principles of the present invention. The present construction is configured to facilitate patency maintenance during intravenous therapy by permitting the catheter assembly to be selectively opened and closed. Additionally, the construction is configured to receive a high molecular weight, viscous fluid, which functions in the nature of a heparin or saline lock to further inhibit ingress of blood into the catheter assembly, which blood can clot or otherwise coagulate and result in patency loss.

The catheter assembly 10 includes a catheter 12 of a generally conventional configuration, with an obturator assembly 14 removably mounted on the catheter 12. While the catheter and obturator assembly can be supplied as a pre-assembled unit, it will be appreciated that the obturator assembly, in accordance with the teachings herein, can be separately supplied for use with pre-existing catheters.

As illustrated, the catheter includes a base portion 16 from which extends a tubular portion 18 defining an internal lumen or passage. The lumen of the tubular portion is in fluid communication with an interior 20 defined by the base portion 16.

The obturator assembly 14 includes a generally annular mounting collar 24 secured to the base portion 16 of the catheter for effecting mounting of the obturator assembly on the catheter. The mounting collar 24 defines an annular mounting socket 26 for receiving the base portion 16, preferably by a friction fit, with the mounting collar further including a central coupling 28 which extends into the base portion 16.

The mounting collar 24 in turn carries a reciprocable obturator member 30. In accordance with the illustrated embodiment, the obturator member 30 comprises a rearward body portion 32, and an elongated obturator rod 34 telescopically disposed within the lumen of the tubular portion of the catheter tubular portion 18. Keyway-like guides 36 defined by the mounting collar 24 respectively receive suitable key-like projections formed on the exterior of the obturator member 30, to thereby guide the reciprocable movement of the obturator member relative to the mounting collar and the catheter 12.

To provide the desired valve-like cooperation between the obturator rod 34 and the tubular portion 18 of the catheter, the obturator rod includes a free end portion having a circular configuration complemental to the circular, cross-sectional configuration of the lumen defined by tubular portion 18. The free end portion of the obturator rod 34 is sized relative to the lumen to provide a sliding seal between the rod and the inside diameter of the tubular portion of the catheter. Thus, when this free end portion of the obturator rod is positioned generally within the free end of the tubular portion 18, they cooperate to inhibit flow of liquid into the tubular portion 18. Thus, flow of blood into the catheter is inhibited, thereby avoiding patency loss.

To accommodate liquid flow through the tubular portion 18, the obturator rod 34 defines at least one, and preferably a plurality, of grooves or recesses which extend axially within the tubular portion 18. In the illustrated embodiment, the obturator rod 34 has a multi-lobular cross-sectional configuration, thereby defining a plurality of grooves 38 which correspond in number to the number of lobes (i.e., three) of the cross-sectional lobular configuration.

Thus, reciprocation of the rod 34 by reciprocation of obturator member 30 relative to mounting collar 24 provides the desired valve-like action. Specifically, the rod 34 is moved between a first, closed position (wherein the free end portion of the rod is retracted and seals the lumen), and a second, open position (wherein the rod is extended so that the grooves 38 are exposed to permit liquid flow through the catheter).

The obturator member 30, and thus the obturator rod 34, are preferably biased so that the rod 34 is biased toward its first, closed position relative to tubular portion 18 of the catheter. In the illustrated embodiment, this biasing action is provided by a generally annular biasing collar 40 operatively connected to the body portion 32 and the mounting collar 24. By this arrangement, the obturator rod can be easily and conveniently moved to its open position, when desired, but is otherwise automatically retained in its closed position.

As noted, patency maintenance provided by the present construction is desirably enhanced by augmenting the valve-like arrangement provided by obturator rod 34 with the provision of a high molecular weight, viscous fluid, within the catheter assembly. By way of example, a fluid such as comprising Dextran in dextrose can be used, although other high viscosity, non-reactive solutions can be employed.

Figure 2:
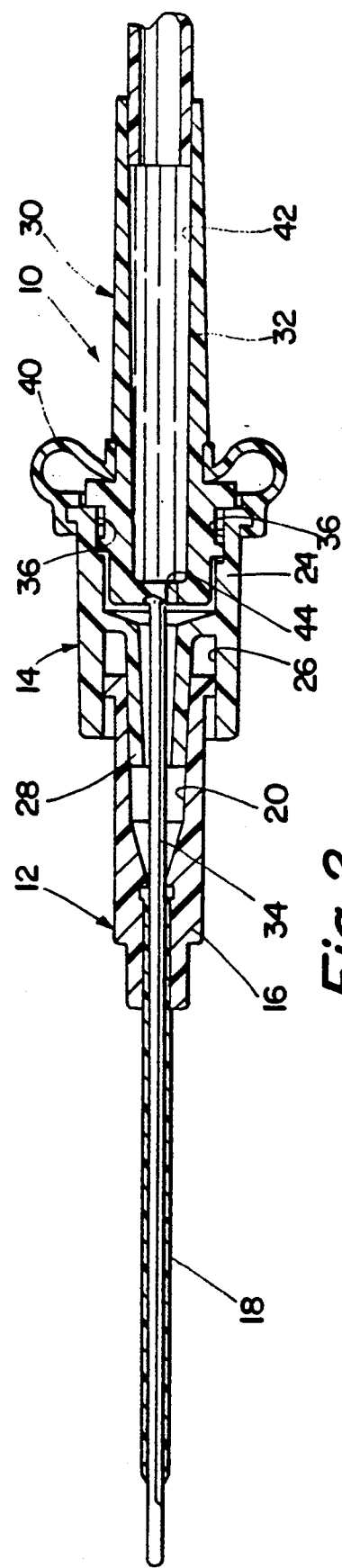
FIG. 2 is a view similar to FIG. 1, illustrating the present catheter assembly in an open position.
Figure 4:
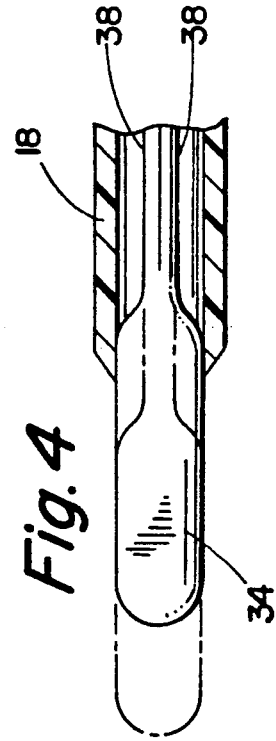
FIG. 4 is a fragmentary, enlarged view of a free end portion of the present catheter assembly.
Figure 3:
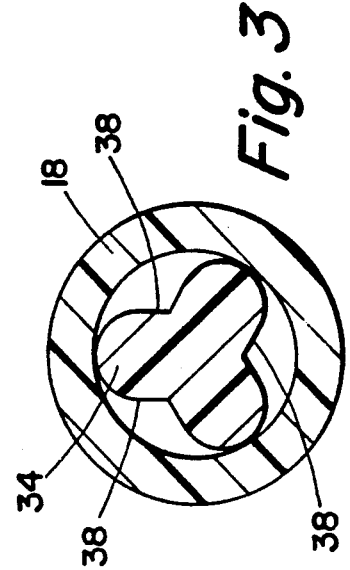
FIG. 3 is a cross-sectional view taken along lines 3—3 of FIG. 1.

The configuration of the present assembly facilitates introduction of such a fluid into the device, such as generally illustrated in FIG. 2. Specifically, the body portion 32 of the obturator member 30 defines an interior cavity 42 which communicates, via a passage 44 and through central coupling 28, with the interior of the base portion 16 of the catheter, and thus communicates with the lumen of the catheter. A suitable protective closure 46 (FIG. 1) can be fitted to the body portion 34 for retaining the selected fluid within the assembly.

In order to effect infusion, the protective cap can be removed, and the obturator rod urged forward by pressing obturator member 30 against the opposition of biasing collar 40. The assembly can then be flushed, followed by infusion of the desired solution into the patient.

Upon completion, the assembly can again be filled with the desired viscous, non-reactive solution, and the obturator member 30 released so that obturator rod 34 is returned to its first, closed position in order to seal the catheter lumen.

Use of the present construction provides distinct advantages over current patency maintenance procedures. It is believed that the present device provides patency that is equivalent to, or better than, that achieved with heparin lock procedures, but avoids the plural flushes required with heparin locks attendant to patient infusion. In addition to offering the ease of use of saline locks, with but a single flush required attendant to infusion, the present device requires fewer flushes with a relatively less expansive flush liquid, thereby desirably acting to lower the cost for the intravenous therapy.

From the foregoing, it will be observed that numerous modifications and variations can be effected without departing from the true spirit and scope of the novel concept of the present invention. No limitation with respect to the specific embodiment illustrated herein is intended or should be inferred. The disclosure is intended to cover all such modifications as fall within the scope of the appended claims.

What is claimed is:

1. A catheter assembly, comprising:
   a catheter including a base portion, and a proximal tubular portion extending from said base portion having a distal free end opposite said base portion and defining a lumen in fluid communication with an interior defined by said base portion;
   obturator means mounted on said catheter for controlling the flow of liquid into said free end of said tubular portion, said obturator means including an elongated obturator rod, having a distal free end, extending telescopically within the lumen of said tubular portion of said catheter for selective reciprocable movement axially of said tubular portion, between a first portion wherein said obturator rod cooperates with said tubular portion to inhibit flow of liquid into the free end of said tubular portion, and a second position wherein liquid can flow through said lumen of said tubular portion and past said obturator rod, wherein said free end portion of said obturator rod has a cross-sectional configuration complemental to the cross-sectional configuration of said lumen of said tubular portion of said catheter for cooperation with said tubular portion for inhibiting liquid flow into said lumen, and said obturator rod further defines at least one axially extending groove means extending axially within said tubular portion for permitting liquid flow through said tubular portion and past said obturator rod in the second position thereof; and biasing means operatively connected to said obturator means for biasing said obturator rod toward said first position.

2. A catheter assembly in accordance with claim 1, wherein
   said obturator rod has a multi-lobular cross-sectional configuration proximal of said free end portion thereof to thereby define a plurality of said groove means corresponding in number to the number of lobes of said cross-sectional configuration of said rod.

3. A catheter assembly in accordance with claim 1, wherein
   said obturator means includes a reciprocable body portion to which said obturator rod is joined for reciprocably moving said rod between said first and second positions, said body portion defining an interior cavity in fluid communication with the interior of said base portion of said catheter so that liquid can flow from said interior cavity into said catheter.

4. A catheter assembly in accordance with claim 3, wherein
   said obturator means further includes mounting means for mounting said obturator means on said base portion of said catheter, said mounting means including means for guiding the reciprocable movement of said obturator rod and said body portion relative to said mounting means.

5. A catheter assembly in accordance with claim 4, wherein
   said obturator means includes biasing means operatively connected to said reciprocable body portion and said mounting means for biasing said obturator rod to said first position.

6. A catheter assembly comprising a catheter having a proximal base portion and a tubular portion having a distal free end opposite said base portion and extending from said base portion and defining a lumen in fluid communication with an interior defined by said base portion and an obturator assembly comprising:
   mounting means for mounting said obturator assembly on the base portion of said catheter;
   an obturator member carried by said mounting means for reciprocable movement relative to said mounting means and the associated catheter, said obturator member comprising a body portion, and an obturator rod, having a distal free end, extending from said body portion for telescopic disposition in the lumen of said tubular portion of said catheter, said obturator member being movable for moving said obturator rod between a first position wherein said obturator rod cooperates with the tubular portion of said catheter to inhibit flow of liquid into the free end of said tubular portion, and a second position wherein said liquid can flow through said lumen of said tubular portion and past said obturator rod; and
   biasing means operatively connected to said obturator member for biasing said obturator rod toward said first position thereof; wherein said body portion of said obturator member defines an interior cavity which can be joined in fluid communication with the lumen of the associated catheter when said obturator assembly is mounted thereon.

7. A catheter assembly in accordance with claim 6, wherein
   said obturator rod has a circular free end portion complemental to the lumen of said catheter for cooperation with said tubular portion for inhibiting liquid flow into said lumen, and said rod further has having a multilobular cross-sectional configuration proximal of said free end portion to thereby define a plurality of groove means extending axially within said tubular portion for permitting liquid flow through said tubular portion and past said obturator rod in the second position thereof, said plurality of groove means corresponding in number to the number of lobes of said cross-sectional configuration of said rod.

* * * * *